US012285533B2

United States Patent
Ishimoto et al.

(10) Patent No.: US 12,285,533 B2
(45) Date of Patent: Apr. 29, 2025

(54) STERILIZER AND MOBILE RADIATION IRRADIATOR

(71) Applicant: Konica Minolta, Inc., Tokyo (JP)

(72) Inventors: Hajime Ishimoto, Hachioji (JP); Makoto Sumi, Tokorozawa (JP)

(73) Assignee: KONICA MINOLTA, INC., Tokyo (JP)

( * ) Notice: Subject to any disclaimer, the term of this patent is extended or adjusted under 35 U.S.C. 154(b) by 401 days.

(21) Appl. No.: 17/816,507

(22) Filed: Aug. 1, 2022

(65) Prior Publication Data

US 2023/0054965 A1    Feb. 23, 2023

(30) Foreign Application Priority Data

Aug. 19, 2021    (JP) .................................. 2021-133940

(51) Int. Cl.
*A61L 2/10*    (2006.01)

(52) U.S. Cl.
CPC ............. *A61L 2/10* (2013.01); *A61L 2202/11* (2013.01); *A61L 2202/14* (2013.01); *A61L 2202/16* (2013.01)

(58) Field of Classification Search
CPC .... A61L 2/10; A61L 2202/11; A61L 2202/14; A61L 2202/16
See application file for complete search history.

(56) References Cited

U.S. PATENT DOCUMENTS

| 11,524,083 | B1* | 12/2022 | Potthast ................ A61L 2/0047 |
| 2016/0074545 | A1* | 3/2016 | Kim ...................... H04R 1/028 |
| | | | 250/455.11 |
| 2017/0303880 | A1 | 10/2017 | Langley et al. |
| 2018/0357385 | A1* | 12/2018 | LaPorte ................... A61L 2/08 |
| 2020/0078483 | A1* | 3/2020 | Eidman ..................... A61L 2/24 |
| 2022/0047229 | A1* | 2/2022 | Takata ................ A61B 6/0414 |
| 2022/0047743 | A1* | 2/2022 | Miller ....................... A61L 2/10 |
| 2023/0054965 | A1* | 2/2023 | Ishimoto .................. A61L 2/10 |

FOREIGN PATENT DOCUMENTS

| JP | H09-253083 | A | | 9/1997 | |
| JP | 2007-097692 | A | | 4/2007 | |
| JP | 2009-290138 | A | | 12/2009 | |
| JP | 2013-248124 | A | | 12/2013 | |
| KR | 20150028162 | A | * | 3/2015 | ............... A61L 2/10 |
| WO | 2016/182024 | A1 | | 11/2016 | |

OTHER PUBLICATIONS

Office Action, dated Mar. 11, 2025, issued for the corresponding Japanese Patent Application No. 2021-133940, 13 pages, with English translation.

* cited by examiner

*Primary Examiner* — David A Vanore
(74) *Attorney, Agent, or Firm* — LUCAS & MERCANTI, LLP (57) ABSTRACT

A sterilizer includes: a holder that holds a portable radiographic imager; and an LED row in which a plurality of LEDs that emit an ultraviolet ray are arranged in a row and which directly or indirectly irradiates a radiation incident surface of the radiographic imager with the ultraviolet ray emitted by each LED, the radiographic imager being held by the holder.

13 Claims, 7 Drawing Sheets

STERILIZER AND MOBILE RADIATION IRRADIATOR

CROSS-REFERENCE TO RELATED APPLICATIONS

The entire disclosure of Japanese Patent Application No. 2021-133940 filed on Aug. 19, 2021 is incorporated herein by reference in its entirety.

BACKGROUND

Technological Field

The invention relates to a sterilizer and a mobile radiation irradiator.

Description of the Related Art

In radiography that is performed using a mobile radiation irradiator (also called a rounding cart) and a portable radiographic imager (flat panel detector: FPD) while making the rounds in a medical facility, it is common to capture an image of a plurality of subjects while reusing the radiographic imager.

For this reason, in the related art, measures have been taken to prevent infection with bacteria or viruses through the radiographic imager, such as capturing an image in a state where the radiographic imager is put in a bag and replacing the bag when moving on to the next image capturing, or wiping a surface of the radiographic imager with a disinfectant every time image capturing is finished.

However, this work has been a large burden on a person that captures an image (radiologist or the like).

In recent years, it has been conceived that a sterilization lamp is provided in a container that contains the radiographic imager in the mobile radiation irradiator, to sterilize and disinfect the contained radiographic imager (for example, refer to JP 2013-248124A).

SUMMARY

However, the sterilization lamp that has been used for the sterilization of the radiographic imager has used mercury. For this reason, there have been concerns about the impact of the sterilization lamp of the related art on the environment during manufacturing or disposal.

In recent years, an ultraviolet LED that can generate a high-energy ultraviolet ray required for sterilization has been developed. For this reason, in the future, it is expected that a light source of the sterilization lamp is replaced with the ultraviolet LED.

On the other hand, the LED is even a point light source, but when the LED is disposed in a narrow place (a large distance between the LED and an irradiation target cannot be taken) such as the container of the radiation irradiator, the irradiation range is very narrow. For this reason, in order to irradiate the radiographic imager with the ultraviolet ray in a planar shape, it is necessary to perform irradiation with the ultraviolet ray from a plurality of locations using a large number of the ultraviolet LEDs.

However, when the number of the ultraviolet LEDs to be used is increased, the electric power consumption increases. For this reason, when the ultraviolet LEDs are used as a sterilization lamp of a mobile radiation generator, there is a possibility that a battery built into the radiation generator cannot supply enough electric power.

In addition, the ultraviolet LEDs have poor energy conversion efficiency and release a large amount of the supplied electric power as heat. For this reason, when a large number of the ultraviolet LEDs are used for sterilization, it is necessary to take measures against heat generation such as a substrate to which the ultraviolet LEDs are attached being made of metal or a heat sink being provided on the back of the substrate. Such measures against heat generation increase the weight of a device.

In addition, since the ultraviolet LEDs are very expensive, the manufacturing cost of the device is increased as the number of the ultraviolet LEDs to be used is increased.

The present invention is conceived in view of the above problems, and an object of the present invention is to enable the sterilization of the entirety of at least a radiation incident surface of a radiographic imager using ultraviolet LEDs while preventing an excessive increase in the electric power consumption, the weight, and the manufacturing cost of a device.

To achieve at least one of the abovementioned objects, according to an aspect of the present invention, a sterilizer reflecting one aspect of the present invention includes: a holder that holds a portable radiographic imager; and an LED row in which a plurality of LEDs that emit an ultraviolet ray are arranged in a row and which directly or indirectly irradiates a radiation incident surface of the radiographic imager with the ultraviolet ray emitted by each LED, the radiographic imager being held by the holder.

According to another aspect, a mobile radiation irradiator configured to be movable includes: a main body; a holder provided in the main body to hold a portable radiographic imager; an LED row in which a plurality of LEDs that emit an ultraviolet ray are arranged in a row and which irradiates a radiation incident surface of the radiographic imager with the ultraviolet ray emitted by each LED, the radiographic imager being held by the holder;

and a radiation source that generates radiation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinbelow, embodiments of the present invention will be described with reference to the drawings. However, the present invention is not limited to those showing in the drawings.

1. First Embodiment

Firstly, a first embodiment of the present invention will be described.

[1-1. Radiographic imager] Initially, an outline of a radiographic imager (hereinbelow, an imager 200) that is sterilized by a sterilizer 100 according to the present embodiment will be described.

Figure 1:
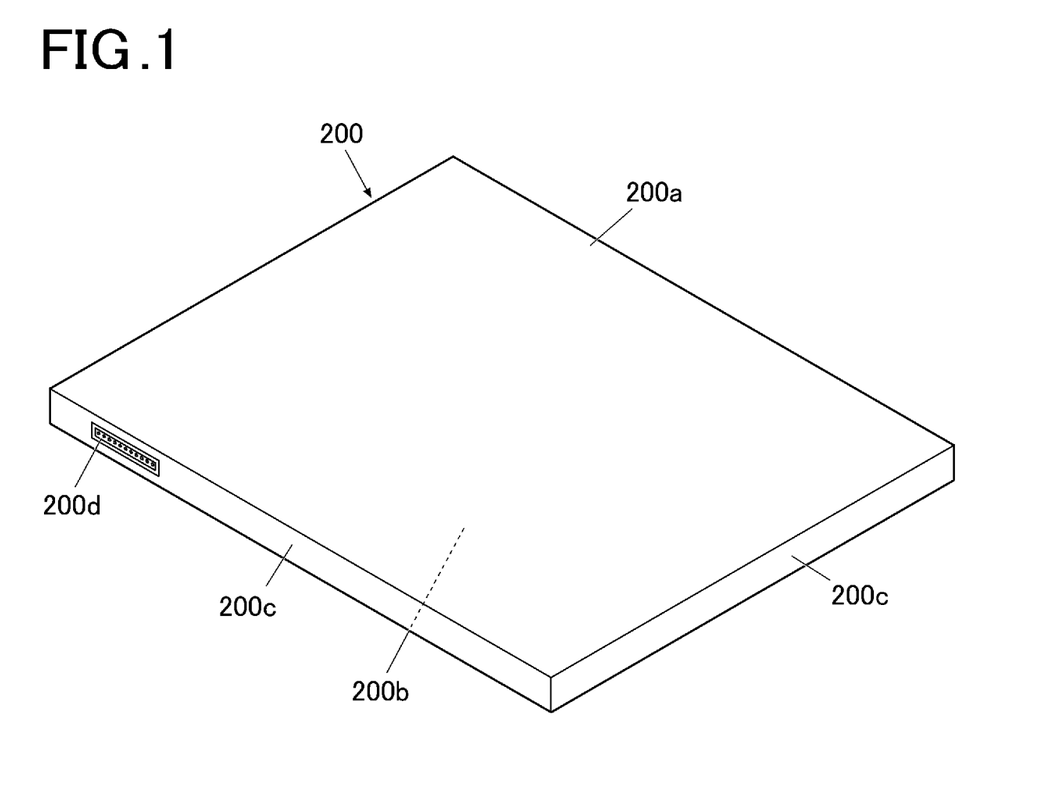
FIG. 1 is a perspective view showing one example of a radiographic imager that is sterilized by a sterilizer according to first to fourth embodiments of the present invention.

FIG. 1 is a perspective view showing one example of the imager 200.

The imager 200 is also sterilized by sterilizers 100A, 100B, and 100C according to second to fourth embodiments.

The imager 200 is portable.

As shown in FIG. 1, the imager 200 according to the present embodiment has, for example, a rectangular panel shape.

In the imager 200 according to the present embodiment, one of a pair of widest rectangular surfaces among six rectangular surfaces forming a surface of the imager 200 is a radiation incident surface (hereinbelow, an incident surface 200a).

Hereinbelow, the other (surface opposite to the incident surface 200a) of the pair of widest rectangular surfaces among the six rectangular surfaces forming the surface of the imager 200 is referred to as a back surface 200b, and surfaces other than the incident surface 200a and the back surface 200b are referred to as side surfaces 200c.

In the imager 200 according to the present embodiment, one side surface 200c of four side surfaces 200c includes a first terminal 200d.

When the incident surface 200a receives radiation, the imager 200 configured in such a manner generates image data of a radiographic image corresponding to a dose distribution of the received radiation.

The imager 200 transmits the generated image data to another device (for example, a mobile radiation irradiator or the like to be described later) via a communication network (wired or wireless).

[1-2. Configuration of sterilizer] Next, a configuration of the sterilizer 100 according to the present embodiment will be described.

Figure 2:
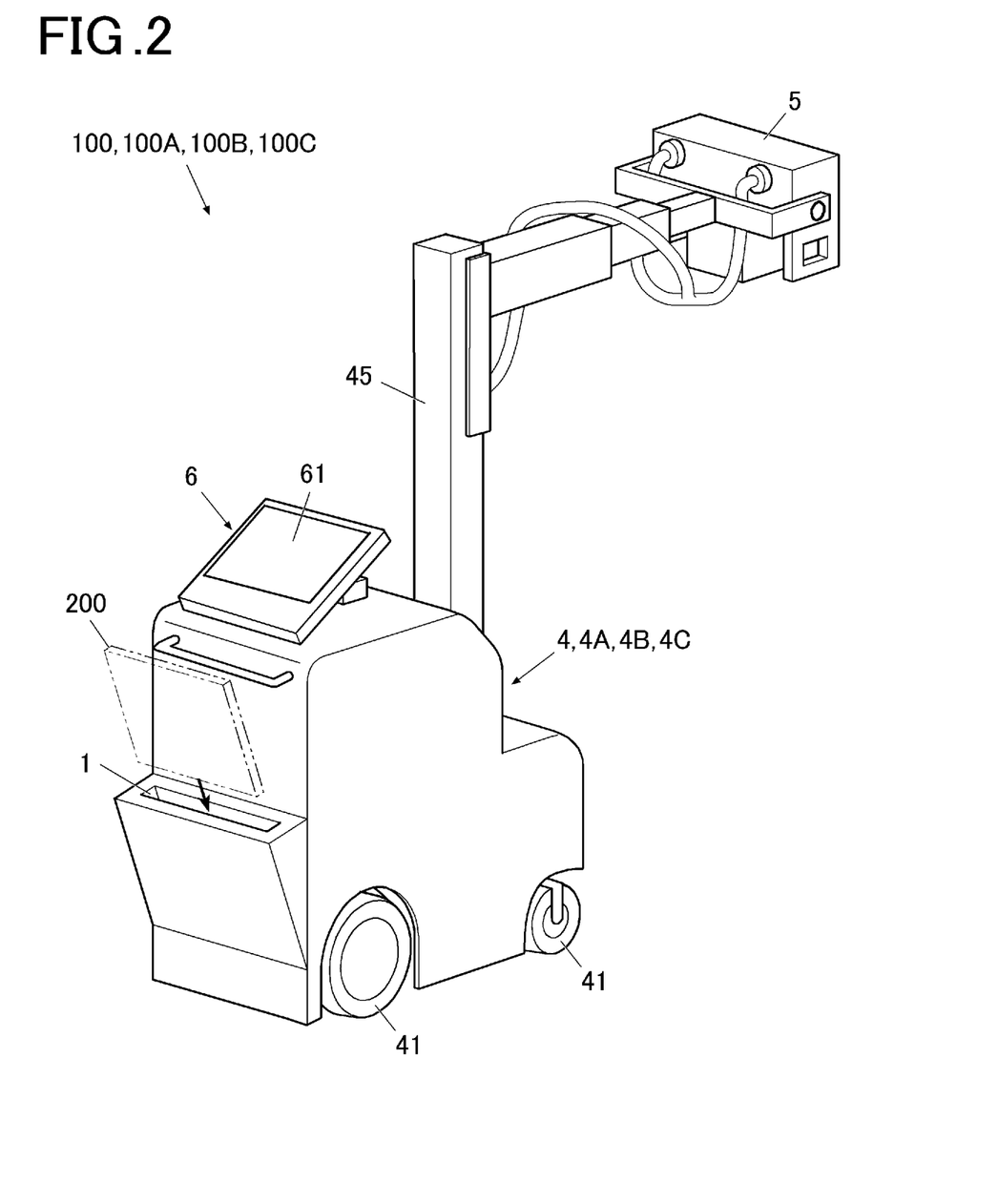
FIG. 2 is a perspective view showing one example of the sterilizer (mobile radiation irradiator) according to the first (second to fourth) embodiments of the present invention.
Figure 3:
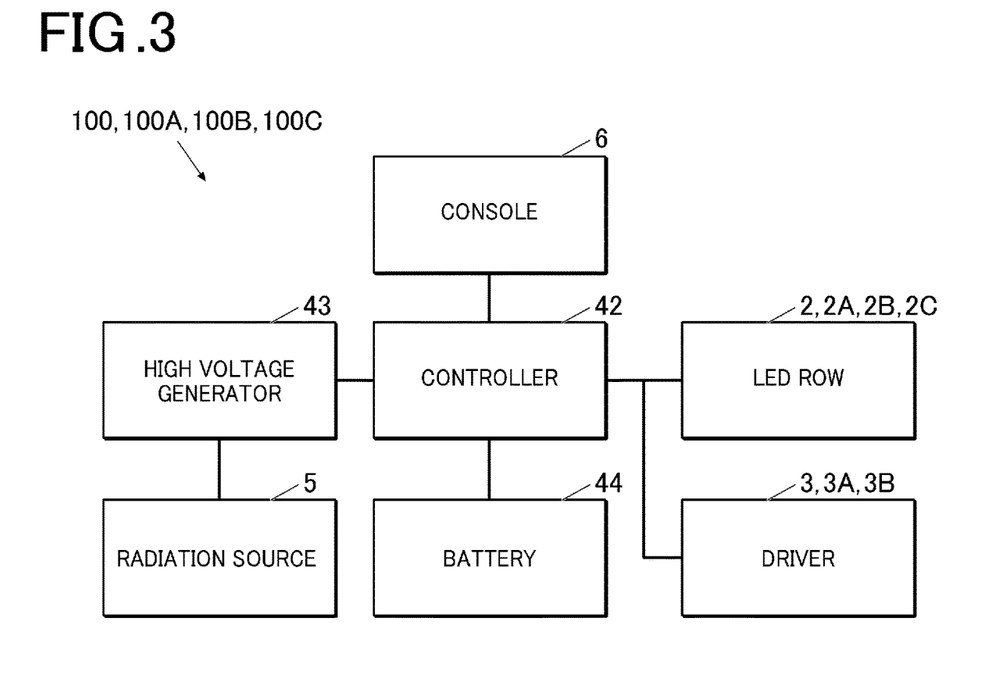
FIG. 3 is a block diagram showing an electrical configuration of the same sterilizer.
Figure 4:
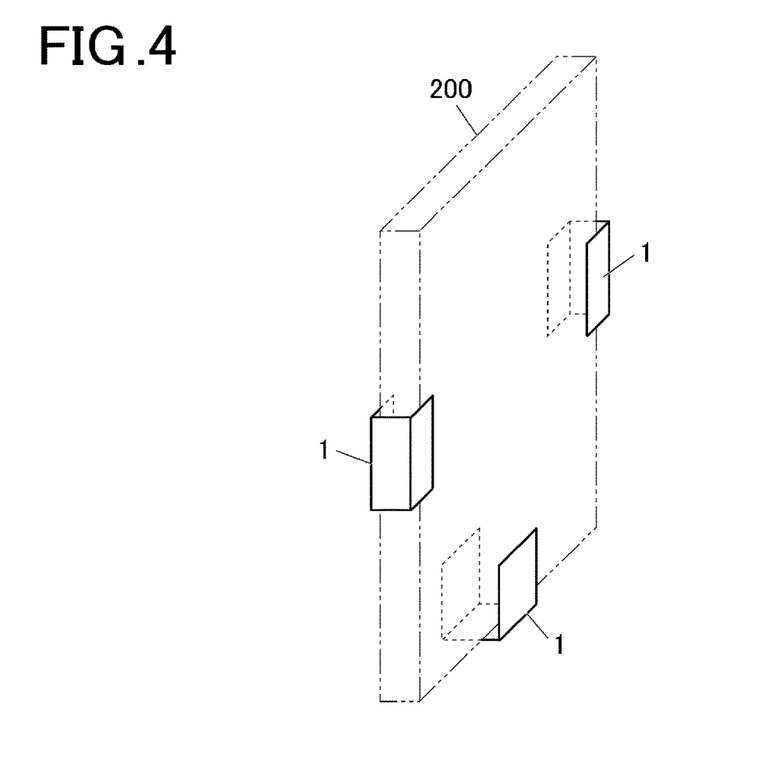
FIG. 4 is a perspective view showing a modification example of a holder provided in the same sterilizer.
Figure 5:
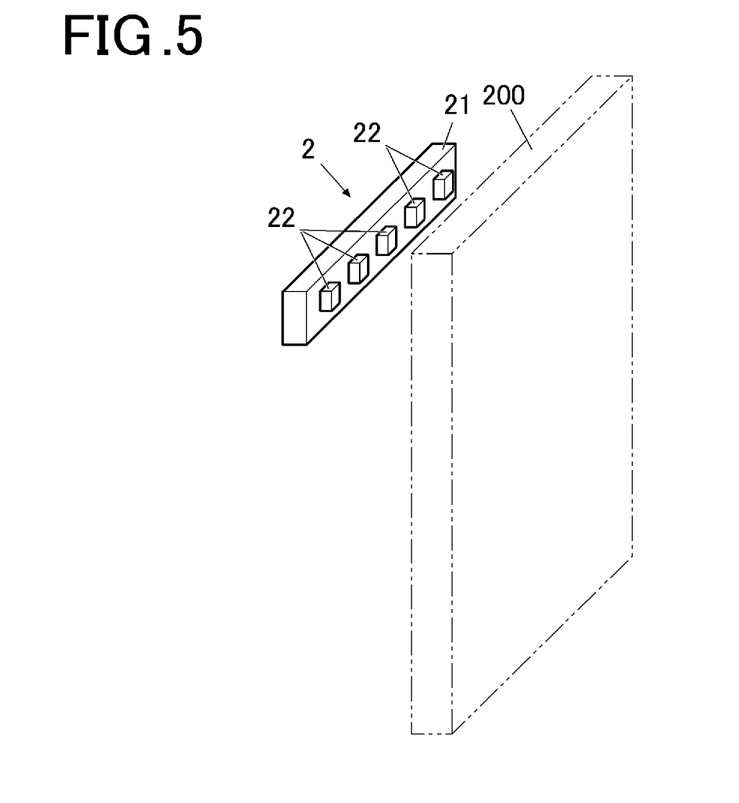
FIG. 5 is a perspective view showing an LED row provided in the same sterilizer.
Figure 6:
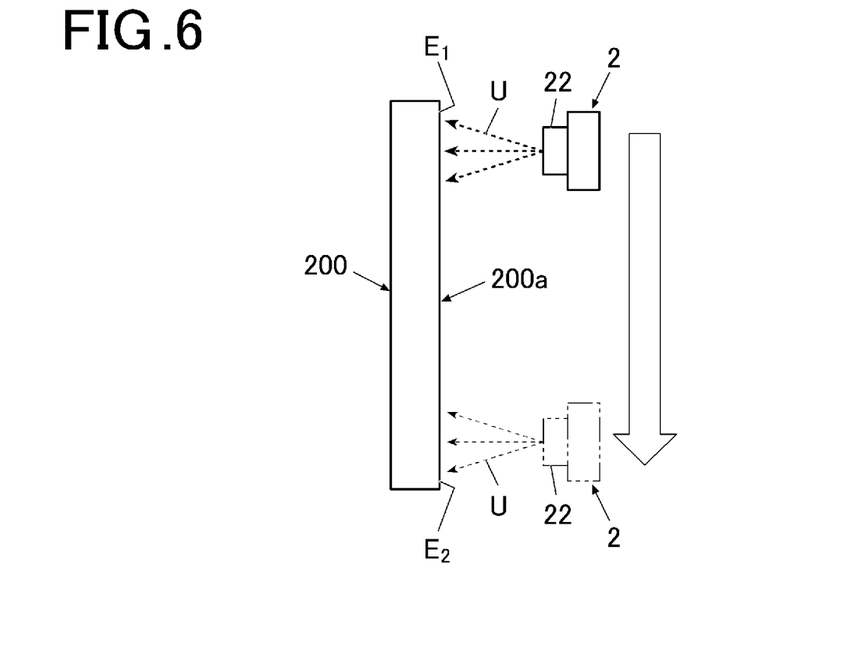
FIG. 6 is a schematic view describing a mode in which the sterilizer according to the first embodiment sterilizes the entirety of a radiation incident surface of the radiographic imager.

FIG. 2 is a perspective view showing one example of the sterilizer 100, FIG. 3 is a block diagram showing an electrical configuration of the same sterilizer, FIG. 4 is a perspective view showing a modification example of a holder provided in the same sterilizer 100, FIG. 5 is a perspective view showing one example of an LED row provided in the same sterilizer 100, and FIG. 6 is a schematic view describing a mode in which the sterilizer 100 sterilizes the entirety of the incident surface 200a.

Parenthesized reference signs in FIGS. 2 and 3 are those of the second to fourth embodiments to be described later.

As shown in FIGS. 2 and 3, the sterilizer 100 includes, for example, a holder 1 and an LED row 2.

The sterilizer 100 according to the present embodiment further includes a first driver 3.

In addition, as shown in FIG. 2, the sterilizer 100 according to the present embodiment is a mobile radiation irradiator (rounding cart) (configured to be movable).

For this reason, the sterilizer 100 according to the present embodiment (hereafter, a rounding cart 100) further includes a main body 4, a radiation source 5, and a console 6.

(1-2-1. Main Body)

The main body 4 is configured to be movable.

The main body 4 according to the present embodiment includes wheels 41. Namely, the rounding cart 100 according to the present embodiment is moved by the rotation of the wheels 41.

In addition, as shown in FIGS. 2 and 3, the main body 4 according to the present embodiment includes a controller 42, a high voltage generator 43, a battery 44, and an arm 45.

These parts 42 to 44 are electrically connected to each other.

The controller 42 controls each part of the rounding cart 100 including the LED row 2 and the first driver 3 based on imaging conditions set on the console 6.

The high voltage generator 43 applies a tube voltage set in advance to the radiation source 5 and energizes the radiation source 5 with a tube current of an amount set in advance for an irradiation time set in advance, based on control from the controller 42.

The battery 44 supplies electric power to the controller 42.

In addition, the battery 44 also supplies electric power to the high voltage generator 43, the LED row 2, the first driver 3, and the imager 200 held by the holder 1, based on a control signal from the controller 42.

The arm 45 forms a front portion of the main body 4 and is provided to extend upward as shown in FIG. 2.

The main body 4 may be movable by a device (for example, by a slippery bottom surface or the like) other than the wheels 41.

(1-2-2. Radiation Source)

The radiation source 5 generates radiation.

The radiation source 5 according to the present embodiment is provided at a tip of the arm 45 of the main body 4.

The radiation source 5 according to the present embodiment generates radiation (for example, X-ray or the like) of a dose corresponding to the tube voltage applied from the high voltage generator 43 and to the energized tube current.

(1-2-3. Console)

In addition, the console 6 sets various imaging conditions (conditions related to a subject (imaging site, imaging direction, physique, and the like), conditions related to irradiation with radiation (imaging mode, still image capturing, motion image capturing, or the like), tube voltage, tube current, irradiation time, current-time product (mAs value), and the like) for at least one of the imager 200 and the main body 4.

In addition, the console 6 can acquire the image data of the radiographic image generated by the imager 200 and save the image data in the console 6 or transmit the image data to another device (PACS, a dynamics analyzer, or the like).

In addition, the console 6 according to the present embodiment includes a display 61.

The display 61 can display imaging conditions, a radiographic image, and the like.

(1-2-4. Holder)

The holder 1 is provided in the main body 4 to be able to hold the imager 200.

The holder 1 according to the present embodiment is provided on a back surface of the main body 4.

In addition, the holder 1 according to the present embodiment is wall surfaces forming a rectangular parallelepiped space that is open upward and that is one size larger than the imager 200.

Namely, the holder 1 according to the present embodiment is configured such that the insertion and removal of the imager 200 is performed by moving the imager 200 in an up-down direction.

In addition, the holder 1 according to the present embodiment includes a second terminal 11 at a position facing the first terminal 200$d$ of the imager 200. When the first terminal 200$d$ of the imager 200 comes into contact with the second terminal 11, the imager 200 is electrically connected to each part of the rounding cart 100.

The holder 1 may be provided on a surface other than the back surface of the main body 4.

In addition, the holder 1 may be configured such that the insertion and removal of the imager 200 is performed by moving the imager 200 in a direction other than the up-down direction.

In addition, the holder 1 may hold the imager 200 horizontally (such that the incident surface 200$a$ face upward or downward).

In addition, as long as the holder 1 can restrict the unnecessary displacement of the imager 200, the holder 1 does not need to be shaped to contain the entirety of the imager 200 as in the present embodiment. Namely, for example, as shown in FIG. 4, the holder 1 may be attached to a wall surface of the main body 4 to lock a part of the imager 200. In that case, it is desirable that the holder 1 is made of a material that does not block ultraviolet rays (for example, resin having a high transparency or the like).

(1-2-5. LED Row)

In the LED row 2, for example, as shown in FIG. 5, a plurality of LEDs 22 that emit an ultraviolet ray U are arranged in a row.

The LED row 2 according to the present embodiment includes a substrate 21 and the plurality of LEDs 22.

The substrate 21 has an elongated belt shape.

The plurality of LEDs 22 are attached to a surface of the substrate 21 to be arranged along a longitudinal direction of the substrate 21.

In addition, the LED row 2 according to the present embodiment is disposed such that each of the LEDs 22 emits the ultraviolet ray U toward the incident surface 200$a$.

Namely, the LED row 2 according to the present embodiment directly irradiates the incident surface 200$a$ of the imager 200 held by the holder 1, with the ultraviolet ray U emitted by each of the LEDs 22.

FIG. 5 shows the LED row 2 in which the plurality of LEDs 22 are arranged in one row, but the LEDs of the LED row 2 may be arranged in a plurality of rows (for example, approximately two or three rows).

(1-2-6. First Driver)

The first driver 3 (refer to FIG. 3) moves the LED row 2 in a direction along the incident surface 200$a$ and orthogonal to a direction in which the plurality of LEDs 22 are arranged.

The first driver 3 is formed of, for example, a ball screw linear motion mechanism, a belt drive shuttle mechanism, or the like.

[1-3. Control of sterilizer] The controller 42 of the main body 4 of the rounding cart 100 configured in such a manner executes the following control.

For example, on the occasion predetermined conditions have been satisfied (for example, the imager 200 has been held by the holder 1, the previous sterilization of the imager 200 has been completed, a predetermined reset operation has been performed, and the like), the controller 42 controls the first driver 3 to move the LED row 2 to a position (a sterilization start position and a position shown by the solid line in FIG. 6) facing one end portion $E_1$ in a direction along one arbitrary side of the incident surface 200$a$ of the imager 200 (for example, a longitudinal direction).

In addition, on the occasion predetermined conditions have been satisfied (for example, the imager 200 has been held by the holder 1, a predetermined sterilization start operation has been performed, and the like), the controller 42 controls the battery 44 to turn on each of the LEDs 22 of the LED row 2.

In addition, on the occasion predetermined conditions have been satisfied (for example, the imager 200 has been held by the holder 1, a predetermined sterilization start operation has been performed, the energization of the LEDs 22 has been started, and the like), the controller 42 controls the first driver 3 to move the LED row 2 at the sterilization start position to a position (a sterilization end position and a position shown by the alternate long and two short dashed line in FIG. 6) facing the other end portion $E_2$ in the direction along the one arbitrary side of the incident surface 200$a$ of the imager 200 at a constant speed.

[1-4. Operation of sterilizer] When the imager 200 is held by the holder 1 of the rounding cart 100 configured in such a manner, first, the sterilization start position is irradiated with a linear ultraviolet ray emitted by the LED row 2. Thereafter, the irradiation position of the ultraviolet ray is moved and finally, the sterilization end position is irradiated with the ultraviolet ray. When the sterilization end position is irradiated with the ultraviolet ray, the entirety of the incident surface 200$a$ is sterilized.

[1-5. Modification examples] The rounding cart 100 may be changed as follows.

Modification Example 1

Figure 7:
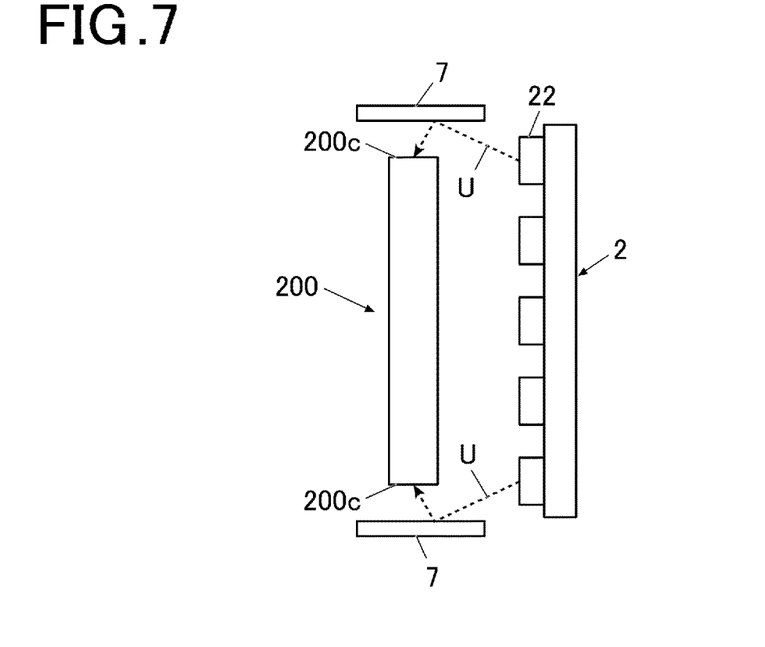
FIG. 7 is a schematic view showing a modification example of the same sterilizer.

For example, the rounding cart 100 may further include, for example, a reflector 7 as shown in FIG. 7.

The reflector 7 reflects the ultraviolet ray U emitted by at least one LED 22 of the LED row 2, toward the side surface 200$c$ of the imager 200.

The reflector 7 is disposed at a position facing the side surface 200$c$ of the imager 200 held by the holder 1.

Specifically, the reflector 7 is disposed at a position facing at least one side surface 200$c$ of the four side surfaces 200$c$ of the imager 200, to extend in the same direction as that of the facing side surface 200$c$ (direction orthogonal to the drawing sheet of FIG. 7 as shown in FIG. 7).

In a case where the reflector 7 is disposed at a position facing at least one of a pair of the side surfaces 200$c$ extending along a movement direction of the LED row 2 (facing rightward or leftward) (state shown in FIG. 7), a part of the side surface 200c facing the reflector 7 is irradiated with the ultraviolet ray from the LED row 2, but when the LED row 2 is moved, the entirety of the side surface 200c is irradiated with the ultraviolet ray.

On the other hand, in a case where the reflector 7 is disposed at a position facing at least one of a pair of the side surfaces 200c extending along a direction orthogonal to the movement direction of the LED row 2 (facing upward or downward), when the LED row 2 is at the sterilization start position or the sterilization end position, the entirety of the side surface 200c facing the reflector 7 is irradiated with the ultraviolet ray U at once.

In such a configuration, not only the incident surface 200a but also the side surface 200c can be sterilized without increasing the LEDs 22 to be used.

Modification Example 2

Figure 8:
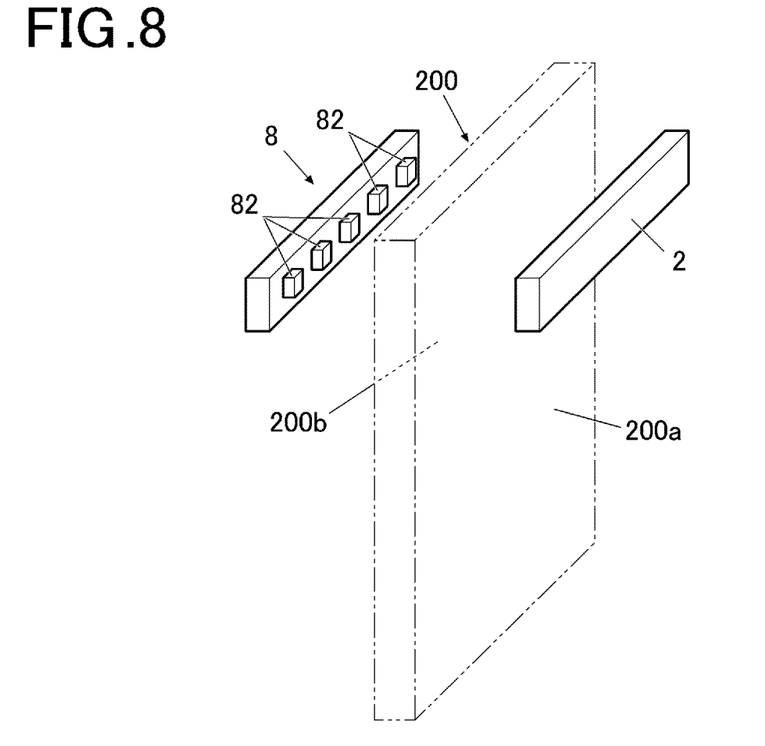
FIG. 8 is a perspective view showing a modification example of the same sterilizer.

In addition, as shown in FIG. 8, the rounding cart 100 may further include a second LED row 8.

In the second LED row 8, similarly to the LED row 2, a plurality of LEDs 82 that emit the ultraviolet ray U are arranged in a row.

The second LED row 8 irradiates the back surface 200b of the imager 200 held by the holder 1, with the ultraviolet ray U emitted by each of the LEDs 82, the back surface 200b being opposite to the incident surface 200a.

The second LED row 8 may be moved together with the LED row 2 by the first driver 3 or may be moved independently of the LED row 2 by another driver different from the first driver 3.

In such a configuration, the rounding cart 100 can sterilize not only the incident surface 200a but also the back surface 200b, for example, without making an and effort of turning the imager 200 front to back after sterilization, holding the imager 200 using the holder 1, and sterilizing the imager 200 again.

A movement direction, a movement speed, a sterilization start position, and the like of the second LED row 8 may be the same as or different from those of the LED row 2.

In addition, the number of the LEDs 82 of the second LED row 8 may be the same as or different from that of the LED row 2.

Modification Example 3

In addition, the rounding cart 100 may calculate an intensity of energy received by the radiation incident surface when irradiated with the ultraviolet ray, based on at least one of a mode of irradiation of the incident surface 200a with the ultraviolet ray U (whether the LED row 2 is moved or a light guiding plate is used (details to be described later), a movement (rotation) speed of the LED row 2, and the like), an intensity of the ultraviolet ray U emitted by each of the LEDs 22, and a range that can be irradiated with the ultraviolet ray U by each of the LEDs 22, and notify about the calculated intensity.

The calculation of the intensity of the energy may be performed by the controller 42 of the main body 4 or may be performed by the console 6 (hardware processor).

In addition, the console 6 may perform the notification of the intensity by displaying the indication on the display 61 or another device may perform the notification of the intensity.

In such a configuration, the rounding cart 100 further includes a calculator and an energy notifier, so that a user can easily identify whether or not the incident surface 200a is irradiated with the ultraviolet ray to be sufficiently sterilized.

Modification Example 4

In addition, the rounding cart 100 may store a cumulative time for which each of the LEDs 22 of the LED row 2 emits the ultraviolet ray U (the LEDs 22 are energized), and notify about an indication of when the cumulative time is more than a predetermined time.

The storage of the cumulative time be performed by the controller 42 of the main body 4 or may be performed by the console 6 (hardware processor).

In addition, the console 6 may perform the notification of an indication of when the cumulative time is more than the predetermined time by displaying the indication on the display 61 or another device may perform the notification of the indication.

In such a configuration, the rounding cart 100 further includes a storage and a time notifier, so that the user can easily estimate the time when the degradation of the LEDs 22 starts.

Modification Example 5

In addition, the rounding cart 100 may measure an intensity of the ultraviolet ray U emitted by each of the LEDs 22 of the LED row 2, and notify about an indication of when the intensity of the ultraviolet ray U is less than a predetermined intensity.

The measurement (quantification of an electric signal from a photodetector (not shown)) of the intensity of the ultraviolet ray U may be performed by the controller 42 of the main body 4 or may be performed by the console 6 (hardware processor).

The console 6 may perform the notification of an indication of when the intensity of the ultraviolet ray U is less than the predetermined intensity by displaying the indication on the display 61 or another device may perform the notification of the indication.

In such a configuration, the rounding cart 100 further includes a measurer and an intensity notifier, so that the user can easily identify whether or not the degradation of the LEDs 22 is started.

In addition, when the calculated intensity of the ultraviolet ray U is less than the predetermined intensity, the rounding cart 100 may perform correction such that the intensity of the energy received by the radiation incident surface 200a of the imager 200 described above is a predetermined intensity or more.

For example, the correction is performed by changing the irradiation time and the like according to a voltage or a current supplied to each of the LEDs 22 or an irradiation mode.

In such a configuration, the rounding cart 100 further includes a corrector, so that even when the intensity of the ultraviolet ray decreases, energy required for sterilization can be secured and the frequency of replacement of the LEDs 22 can also be reduced.

When the rounding cart 100 performs the correction, the rounding cart 100 may notify the user of a correction situation.

In addition, the user may be able to set a value of the predetermined intensity or whether or not the rounding cart 100 automatically performs the correction.

2. Second Embodiment

Next, a second embodiment of the present invention will be described.

Figure 9:
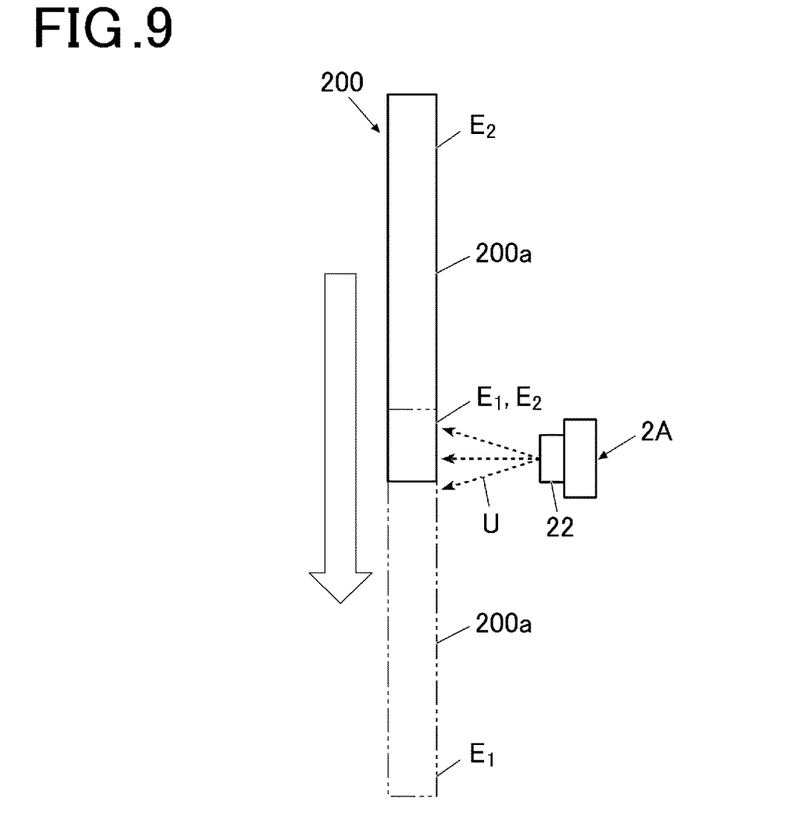
FIG. 9 is a schematic view describing a mode in which the sterilizer according to the second embodiment sterilizes the entirety of the radiation incident surface of the radiographic imager.

FIG. 9 is a schematic view describing a mode in which a sterilizer 100A according to the present embodiment sterilizes the entirety of the incident surface 200a.

The same configurations in the present embodiment as those of the first embodiment are also denoted by the same reference signs, and a detailed description thereof will be omitted.

Similarly to the sterilizer 100 according to the first embodiment, the sterilizer 100A according to the present embodiment is a mobile radiation irradiator (rounding cart).

For this reason, the sterilizer 100A according to the present embodiment is hereinbelow referred to as a rounding cart 100A.

[2-1. Configuration differences] The rounding cart 100A according to the present embodiment does not include the first driver 3 provided in the rounding cart 100 according to the first embodiment.

An LED row 2A according to the present embodiment is fixed at a predetermined position at which each of the LEDs 22 emits the ultraviolet ray U toward the incident surface 200a.

Namely, similarly to the first embodiment, the LED row 2A according to the present embodiment directly irradiates the incident surface 200a of the imager 200 held by the holder 1, with the ultraviolet ray U emitted by each of the LEDs 22.

In addition, as shown in FIG. 3, the rounding cart 100A according to the present embodiment further includes a second driver 3A.

The second driver 3A moves the imager 200 in the direction along the incident surface 200a and orthogonal to the direction in which the plurality of LEDs 22 are arranged.

[2-2. Control differences] On the occasion predetermined conditions have been satisfied, for example, as shown in FIG. 9, a controller 42A of a main body 4A according to the present embodiment controls the second driver 3A to move the imager 200 located at a position at which the one end portion $E_1$ of the incident surface 200a faces the LED row 2A (a sterilization start position and a position shown by the solid line in FIG. 9), to a position at which the other end portion $E_2$ of the incident surface 200a faces the LED row 2A (a sterilization end position and a position indicated by the alternate long and two short dashed line in FIG. 9) at a constant speed.

[2-3. Operation of sterilizer] When the imager 200 is held by the holder 1 of the rounding cart 100A configured in such a manner, first, the sterilization start position is irradiated with a linear ultraviolet ray emitted by the LED row 2A. Thereafter, the irradiation position of the ultraviolet ray is moved and finally, the sterilization end position is irradiated with the ultraviolet ray. When the sterilization end position is irradiated with the ultraviolet ray, the entirety of the incident surface 200a is sterilized.

[2-4. Modification examples] The rounding cart 100A may further include at least one configuration of Modification Examples 1 to 5 of the first embodiment.

3. Third Embodiment

Next, a third embodiment of the present invention will be described.

Figure 10:
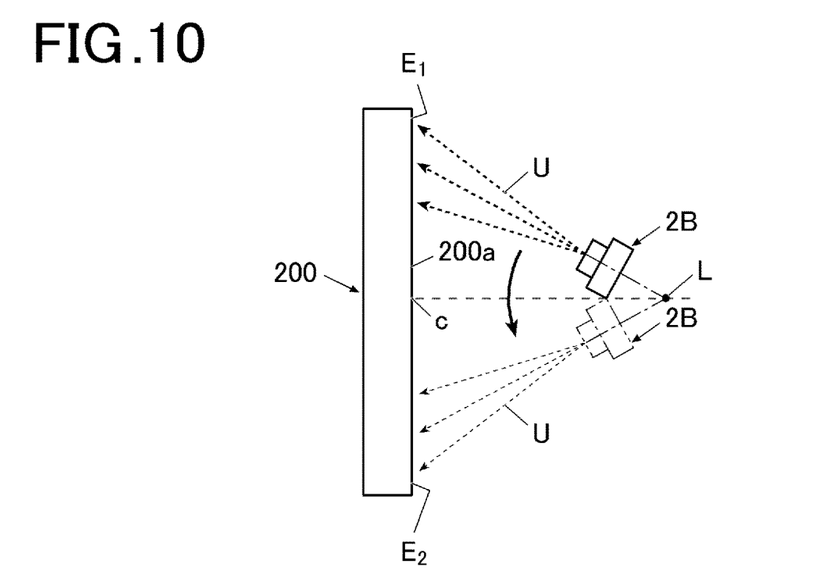
FIG. 10 is a schematic view describing a mode in which the sterilizer according to the third embodiment sterilizes the entirety of the radiation incident surface of the radiographic imager.

FIG. 10 is a schematic view describing a mode in which a sterilizer 100B according to the present embodiment sterilizes the entirety of the incident surface 200a.

The same configurations in the present embodiment as those of the first embodiment are also denoted by the same reference signs, and a detailed description thereof will be omitted.

Similarly to the sterilizer 100 according to the first embodiment, the sterilizer 100B according to the present embodiment is a mobile radiation irradiator (rounding cart).

For this reason, the sterilizer 100B according to the present embodiment is hereinbelow referred to as a rounding cart 100B.

[3-1. Configuration differences] The rounding cart 100B according to the present embodiment does not include the first driver 3 provided in the rounding cart 100 according to the first embodiment.

An LED row 2B according to the present embodiment is disposed such that the LEDs 22 are arranged along the incident surface 200a.

For example, as shown in FIG. 10, the LED row 2B according to the present embodiment is disposed such that the LEDs are arranged along a straight line L passing through a center C of the incident surface 200a and being parallel to one side of the incident surface 200a (extending horizontally or vertically (direction orthogonal to the drawing sheet of FIG. 10)).

In addition, as shown in FIG. 3, the rounding cart 100B according to the present embodiment further includes a third driver 3B.

As shown in FIG. 10, the third driver 3B rotates the LED row 2B around the straight line L as a rotation axis, the straight line L extending along the direction in which the plurality of LEDs 22 are arranged.

FIG. 10 shows a case where the LED row 2B and the straight line L are separated from each other, but the straight line L may pass through the LED row 2B (the LED row 2B may rotates without a change in position).

[3-2. Control differences] As shown in FIG. 10, on the occasion predetermined conditions have been satisfied, a controller 42B of a main body 4B according to the present embodiment controls the third driver 3B to rotate the LED row 2B in which each of the LEDs 22 faces a direction in which the one end portion $E_1$ of the incident surface 200a exists (a sterilization start direction and a direction shown by the solid line in FIG. 10), until each of the LEDs 22 faces a direction in which the other end portion $E_2$ of the incident surface 200a exists (a sterilization end direction and a direction shown by the alternate long and two short dashed line in FIG. 10).

Namely, similarly to the first and second embodiments, the LED row 2B according to the present embodiment also directly irradiates the incident surface 200a of the imager 200 held by the holder 1, with the ultraviolet ray U emitted by each of the LEDs 22.

When the LED row 2B is disposed as in the present embodiment, there is a possibility that the ultraviolet ray U with which the one end portion $E_1$ or the other end portion $E_2$ of the incident surface 200a is irradiated is more diffused than the ultraviolet ray U with which a central portion of the incident surface 200a is irradiated. For this reason, the rotation speed may be changed according to the direction of the LED row 2B to uniformly irradiate the entirety of the incident surface 200a with the ultraviolet ray U.

[3-3. Operation of sterilizer] When the imager 200 is held by the holder 1 of the rounding cart 100B configured in such a manner, first, a linear ultraviolet ray emitted by the LED row 2B is irradiated toward the sterilization start direction. Thereafter, the irradiation position of the ultraviolet ray is changed and finally, the ultraviolet ray is irradiated toward the sterilization end direction. When the ultraviolet ray is irradiated toward the sterilization end direction, the entirety of the incident surface 200a is sterilized.

[3-4. Modification example] The rounding cart 100B may further include at least one configuration of Modification Examples 1 to 5 of the first embodiment.

4. Fourth Embodiment

Next, a fourth embodiment of the present invention will be described.

Figure 11:
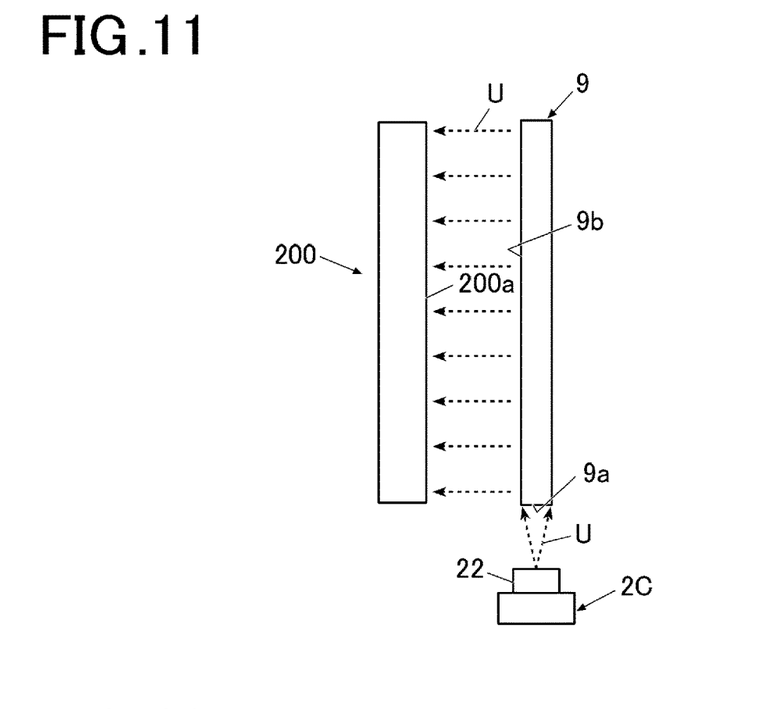
FIG. 11 is a schematic view describing a mode in which the sterilizer according to the fourth embodiment sterilizes the entirety of the radiation incident surface of the radiographic imager.

FIG. 11 is a schematic view describing a mode in which a sterilizer 100C according to the present embodiment sterilizes the entirety of the incident surface 200a.

The same configurations in the present embodiment as those of the first embodiment are also denoted by the same reference signs, and a detailed description thereof will be omitted.

Similarly to the sterilizer 100 according to the first embodiment, the sterilizer 100C according to the present embodiment is a mobile radiation irradiator (rounding cart).

For this reason, the sterilizer 100C according to the present embodiment is hereinbelow referred to as a rounding cart 100C.

[4-1. Configuration differences] The rounding cart 100C according to the present embodiment does not include the first driver 3 provided in the rounding cart 100 according to the first embodiment.

As shown in FIG. 11, the rounding cart 100C according to the present embodiment further includes a light guiding plate 9.

The light guiding plate 9 has a plate shape and diffuses linear light incident from a side surface 9a, to emit the light in a planar shape from a main surface 9b.

In addition, the light guiding plate 9 is disposed such that the main surface 9b of the light guiding plate 9 faces the incident surface 200a of the imager 200 held by the holder 1.

An LED row 2C according to the present embodiment is disposed such that each of the LEDs 22 emits the ultraviolet ray U toward the side surface 9a of the light guiding plate 9.

Namely, unlike the first to third embodiments, the LED row 2C according to the present embodiment indirectly (through the light guiding plate 9) irradiates the incident surface 200a of the imager 200 held by the holder 1, with the ultraviolet ray U emitted by each of the LEDs 22.

[4-2. Control differences] A controller 42C (refer to FIG. 3) of a main body 4C according to the present embodiment does not have a function of controlling the driver.

[4-3. Operation of sterilizer] When the imager 200 is held by the holder 1 of the rounding cart 100C configured in such a manner, the ultraviolet ray diffused in the light guiding plate 9 is irradiated in a planar shape from the main surface 9b. Namely, the entirety of the incident surface 200a is immediately sterilized.

[4-4. Modification example] The rounding cart 100C may further include at least one configuration of Modification Examples 1 to 5 of the first embodiment.

5. Effects

The rounding carts (sterilizers) 100, 100A, 100B, and 100C described above include the holder 1 that can hold the portable imager 200, and the LED rows 2, 2A, 2B, and 2C in each of which the plurality of LEDs 22 that emit the ultraviolet ray U are arranged in a row and which directly or indirectly irradiates the incident surface 200a of the imager 200 held by the holder 1, with the ultraviolet ray U emitted by each of the LEDs 22.

For this reason, according to the rounding carts 100, 100A, 100B, and 100C, the sterilization of the entirety of the incident surface 200a can be performed using the LEDs 22 while preventing an excessive increase in the electric power consumption, the weight, and the manufacturing cost of the rounding carts.

6. Others

The present invention has been described above based on the embodiments, but the present invention is not limited to the embodiments and, needlessly to say, can be appropriately changed without departing from the concept of the present invention.

Figure 12:
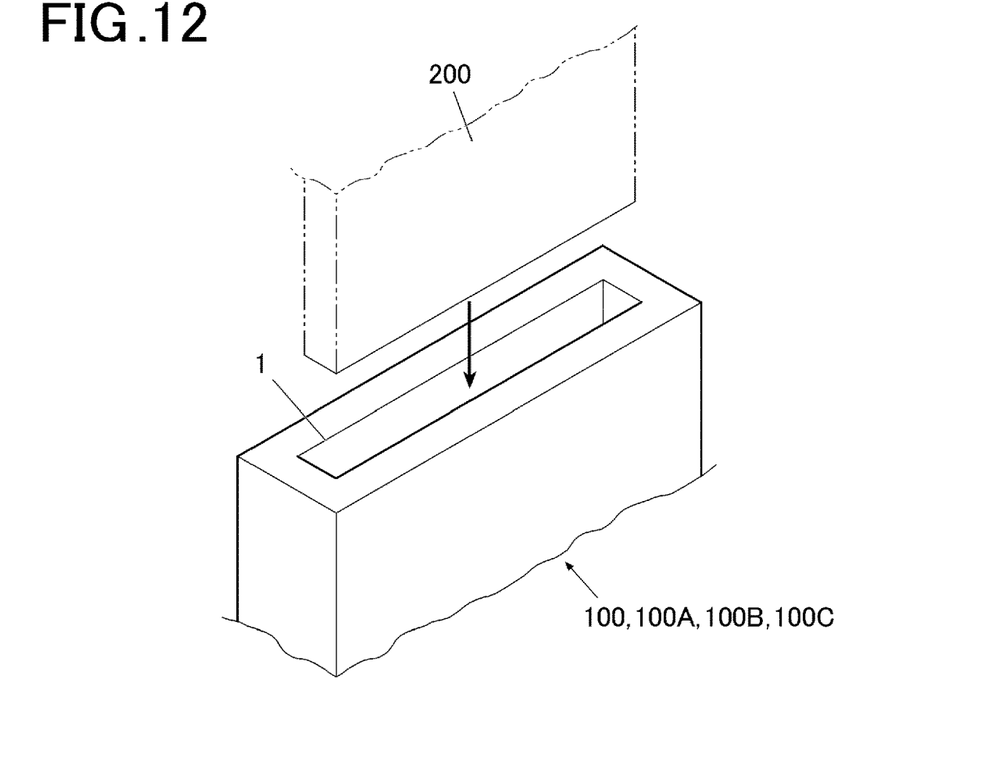
FIG. 12 is a perspective view showing one example of a sterilizer according to another embodiment of the present invention.

For example, in the first to fourth embodiments, the sterilizers 100, 100A, 100B, and 100C that are mobile radiation irradiators (rounding carts) have been provided as an example, but as shown in FIG. 12, the sterilizers 100, 100A, 100B, and 100C according to the present invention may be single devices that do not have a function of performing irradiation with radiation.

In that case, the sterilizers 100, 100A, 100B, and 100C may serve as a charger that charges a built-in battery of the imager 200 held by the holder 1 or a cradle that relays the transfer of image data from the imager 200 held by the holder 1 to another device.

In addition, in the first to fourth embodiments, the sterilizers 100, 100A, 100B, and 100C that perform sterilization using the LED rows 2, 2A, 2B, and 2C in each of which the plurality of LEDs 22 are arranged in a row, but the sterilizers may include the LEDs 22 that do not form one to several rows, and include a device that can cause the entirety of the incident surface 200a of the imager 200 held by the holder 1, to be irradiated with the ultraviolet ray U emitted by the LEDs 22.

This device may be, for example, a fourth driver that moves the LEDs 22 or the imager 200 relatively along the incident surface 200a in a direction along one arbitrary side of the incident surface 200a and in a direction orthogonal to this direction.

In addition, this device may include the same light guiding plate 9 as in the fourth embodiment, and a light pipe having a rod shape that is disposed such that a side surface of the light pipe faces the side surface 9a of the light guiding plate 9 and that diffuses dotted light incident form an end surface of the light pipe to emit the light linearly from a side surface of the light pipe.

In addition, in the first to fourth embodiments, the controllers 42, 42A, 42B, and 42C execute control of the LED rows 2, 2A, 2B, and 2C and of the first to third drivers 3, 3A, and 3B, but the console 6 may execute the control.

In addition, in the first to fourth embodiments, the sterilizers 100, 100A, 100B, and 100C that automatically perform the movement of the LED rows 2 and 2A or the rotation of the LED row 2B, but the sterilizers may manually perform the movement of the LED rows 2 and 2A and the rotation of the LED row 2B.

Although embodiments of the present invention have been described and illustrated in detail, the disclosed embodiments are made for purposes of illustration and example only and not limitation. The scope of the present invention should be interpreted by terms of the appended claims

What is claimed is:

1. A sterilizer comprising:
a holder that holds a portable radiographic imager; and
an LED row in which a plurality of LEDs that emit an ultraviolet ray are arranged in a row and which directly or indirectly irradiates a radiation incident surface of the radiographic imager with the ultraviolet ray emitted by each LED, the radiographic imager being held by the holder.

2. The sterilizer according to claim 1,
wherein the LED row is disposed such that each LED emits the ultraviolet ray toward the radiation incident surface, and
a first driver is further provided that moves the LED row in a direction along the radiation incident surface and orthogonal to a direction in which the plurality of LEDs are arranged.

3. The sterilizer according to claim 1,
wherein the LED row is fixed at a predetermined position such that each LED emits the ultraviolet ray toward the radiation incident surface, and
a second driver is further provided that moves the radiographic imager in a direction along the radiation incident surface and orthogonal to a direction in which the plurality of LEDs are arranged.

4. The sterilizer according to claim 1,
wherein the LED row is disposed such that each LED is arranged along the radiation incident surface, and
a third driver is further provided that rotates the LED row around a straight line as a rotation axis, the straight line extending along a direction in which the plurality of LEDs are arranged.

5. The sterilizer according to claim 1, further comprising:
a light guiding plate having a plate shape, that is disposed such that a main surface of the light guiding plate faces the radiation incident surface of the radiographic imager held by the holder, and that diffuses linear light incident from a side surface of the light guiding plate to emit the light in a planar shape from the main surface; and
the LED row is disposed such that each LED emits the ultraviolet ray toward the side surface of the light guiding plate.

6. The sterilizer according to claim 1, further comprising:
a reflector that reflects the ultraviolet ray emitted by at least one LED of the LED row, toward a side surface of the radiographic imager.

7. The sterilizer according to claim 1, further comprising:
a second LED row in which a plurality of LEDs that emit an ultraviolet ray are arranged in a row and which irradiates a back surface of the radiographic imager held by the holder with the ultraviolet ray emitted by each LED, the back surface being opposite to the radiation incident surface.

8. The sterilizer according to claim 1, further comprising:
a display configured to show an intensity of energy received by the radiation incident surface when irradiated with the ultraviolet ray, which is calculated based on at least one of a mode of irradiation of the radiation incident surface with the ultraviolet ray, an intensity of the ultraviolet ray emitted by each LED, and a range irradiated with the ultraviolet ray by each LED.

9. The sterilizer according to claim 8,
wherein the display is configured to show a corrected intensity, and
the corrected intensity has been corrected such that the intensity of the energy received by the radiation incident surface is a predetermined intensity or more, when the calculated intensity is less than the predetermined intensity.

10. The sterilizer according to claim 1, further comprising:
a display configured to show an indication of when a cumulative time, for which each LED of the LED row emits the ultraviolet ray, is more than a predetermined time.

11. The sterilizer according to claim 1, further comprising:
a display configured to show an indication of when an intensity of the ultraviolet ray emitted by each LED of the LED row
is less than a predetermined intensity.

12. A sterilizer comprising:
a holder that holds a portable radiographic imager; and
an LED that emits an ultraviolet ray; and
a device that causes an entirety of a radiation incident surface of the radiographic imager held by the holder, to be irradiated with the ultraviolet ray emitted by the LED.

13. A mobile radiation irradiator configured to be movable, the irradiator comprising:
a main body;
a holder provided in the main body to hold a portable radiographic imager;
an LED row in which a plurality of LEDS that emit an ultraviolet ray are arranged in a row and which irradiates a radiation incident surface of the radiographic imager with the ultraviolet ray emitted by each LED, the radiographic imager being held by the holder; and
a radiation source that generates radiation.

* * * * *